United States Patent
Mueller et al.

(10) Patent No.: US 7,119,219 B2
(45) Date of Patent: Oct. 10, 2006

(54) ORGANOMETALLIC BUILDING MATERIALS AND METHOD FOR PRODUCING THE SAME

(75) Inventors: Ulrich Mueller, Neustadt (DE); Michael Hesse, Worms (DE); Lisa Lobree, Mannheim (DE); Markus Hoelzle, Kirchheim (DE); Jan-Dirk Arndt, Mannheim (DE); Peter Rudolf, Landenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 389 days.

(21) Appl. No.: 10/469,826

(22) PCT Filed: Mar. 7, 2002

(86) PCT No.: PCT/EP02/02523

§ 371 (c)(1),
(2), (4) Date: Sep. 5, 2003

(87) PCT Pub. No.: WO02/070526

PCT Pub. Date: Sep. 12, 2002

(65) Prior Publication Data

US 2004/0097724 A1 May 20, 2004

(30) Foreign Application Priority Data

Mar. 8, 2001 (DE) .............................. 101 11 230

(51) Int. Cl.
*C07F 3/06* (2006.01)
*C07F 15/00* (2006.01)
*B01J 31/00* (2006.01)

(52) U.S. Cl. .................... 556/118; 556/136; 502/150
(58) Field of Classification Search ............... 556/118, 556/136; 502/150
See application file for complete search history.

(56) References Cited

U.S. PATENT DOCUMENTS 5,648,508 A 7/1997 Yaghi ........................ 556/9

2004/0097724 A1 5/2004 Mueller et al.

FOREIGN PATENT DOCUMENTS

| DE | 35 35 128 | 4/1987 |
|---|---|---|
| DE | 37 22 891 | 1/1989 |
| DE | 38 04 162 | 8/1989 |
| DE | 195 44 450 | 6/1997 |
| EP | 0 790 253 | 8/1997 |
| EP | 1 050 510 | 6/1998 |
| WO | 99 05151 | 2/1999 |

OTHER PUBLICATIONS

XX Zhang et al.: "Coopreative magnetic behavior in the coordination polymers CU3(TMA)2L3 (L=H2O, Pyridine)" Journal of Applied Physics, vol. 87, No. 9, pp. 6007-6009 May 1, 2000.
SA Bourne et al.: "1-D coordination polymers containing benzenedicarboxylate" Crystal Engineering, vol. 4, No. 1, pp. 25-36 Mar. 2001.
Yaghi et al.: "Selective binding and removal of guests in a microporous metal-organic framework" NATURE, vol. 378, No. 6558, pp. 703-706 Dec. 14, 1995.
M. O'Keeffe et al.: "Frameworks for extended solids: geometrical design principles" J. Solid State Chem., vol. 152, pp. 3-20 2000.
Chemical Abstracts, vol. 94, No. 13 156247.
U.S. Appl. No. 10/983,629, filed Nov. 9, 2004, Hesse et al.
Sing, K. S. W., et al., "Reporting Physisorption Data For Gas/Solid Systems with Special Reference to the Determination of Surface Area and Porosity," Pure & Appl. Chem., vol. 57, No. 4, pp. 603-619, 1985.

*Primary Examiner*—Porfirio Nazario-Gonzalez
(74) *Attorney, Agent, or Firm*—Oblon, Spivak, McClelland, Maier & Neustadt, P.C.

(57) ABSTRACT

An organometallic framework material is prepared by a process which comprises reacting a fluid mixture comprising a metal salt with at least one at least bidentate organic compound capable of coordination to metal ions in the presence of at least one base and a solvent, where the solvent comprises at least one cyclic amide (lactam) and/or at least one cyclic ester (lactone).

4 Claims, 1 Drawing Sheet

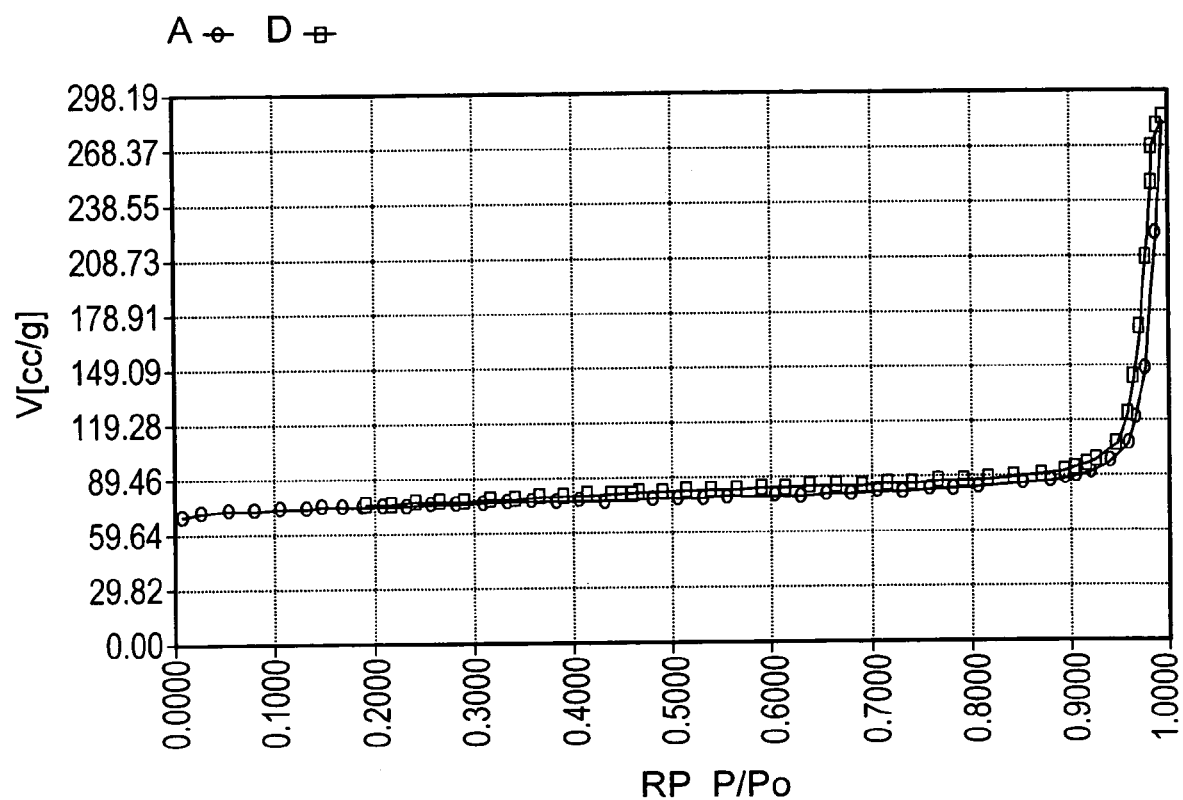

ORGANOMETALLIC BUILDING MATERIALS AND METHOD FOR PRODUCING THE SAME

The present invention relates to novel organometallic framework materials, a process for preparing them and their use as adsorbents, desiccants, flame retardants, storage materials or depot materials for active substances or catalysts.

Organometallic framework materials are known per se. On this subject, we refer to the scientific publication by Yaghi et al. in J. Solid State Chem., Vol. 152 (1), 3–20, which summarizes developments to date in this technical field. A process for preparing such materials is described in EP-A 0790253. The process claimed there for preparing a microporous material comprises mixing a solution comprising at least one metal ion as defined therein with a ligand having substructures containing multidentate functional groups in the presence of a template compound as defined therein. As an application for such materials, this publication makes mention of a process for removing impurities from gases and liquids. Further uses of the material described there are neither mentioned nor suggested in this publication. The process described there, which was carried out using only very small amounts, gives yields, e.g. for zinc terephthalate frameworks, of less than 70%, which are unsatisfactory for the industrial-scale production of such materials. An industrially relevant method of preparation giving high yields as are required, for instance, for use of organometallic framework materials as catalysts is described neither there nor in the other prior art.

It is an object of the present invention to provide a process for preparing such framework materials which, firstly, makes it possible to prepare such materials on an industrial scale in high yields and, secondly, also leads to materials which are new in principle.

We have found that this object is achieved by using N-methylpyrrolidone as solvent or as solvent component for preparing organometallic framework substances. The framework substances can be prepared in high yields in this way.

The present invention accordingly provides a process for preparing an organometallic framework material, which comprises reacting a fluid mixture, e.g. a solution or suspension, comprising a metal salt with at least one at least bidentate organic compound capable of coordination to metal ions in the presence of at least one base and a solvent, where the solvent comprises at least one cyclic amide (lactam) and/or at least one cyclic ester (lactone), e.g. N-methylpyrrolidone, provides an organometallic, microporous framework material comprising a metal ion and at least one at least bidentate organic compound coordinately bound thereto, capable of being prepared by a process which comprises reacting a fluid mixture, e.g. a solution or suspension, comprising a metal salt with at least one at least bidentate organic compound capable of coordination to metal ions in the presence of at least one base and a solvent, where the solvent comprises at least one cyclic amide (lactam) and/or at least one cyclic ester (lactone), e.g. N-methylpyrrolidone, and provides for the use of the organometallic framework material as catalyst, adsorbent, desiccant, flame retardant, storage material, depot material for active substances, sensor material, pigment or electronic component.

Possible metal components within the metal salt used according to the present invention are the elements of groups Ia, IIa, IIIa, IVa–VIIIa and Ib–VIb of the Periodic Table, with particular preference being given to zinc, copper, nickel, palladium, platinum, ruthenium, rhenium and cobalt.

As at least bidentate organic compound capable of coordination to metal ions, it is in principle possible to use all compounds which are suitable for this purpose and meet the above conditions. The organic compound has to have, in particular, at least two centers which can form a bond with the metal ions of a metal salt, in particular with the metals of the abovementioned groups Ia, IIa, IIIa, IVa–VIIIa and Ib–VIb. These can be selected from among, in particular:

substituted and unsubstituted, monocyclic and polycyclic aromatic dicarboxylic acids and substituted and unsubstituted, monocyclic and polycyclic aromatic dicarboxylic acids containing at least one heteroatom.

Specific examples are:

dicarboxylic acids of benzene, naphthalene, pyridine or quinoline.

The solvent used in the process of the present invention is a solvent which comprises a cyclic amide and/or a cyclic ester, either alone or together with a suitable cosolvent. Suitable cosolvents are in principle all protic and/or aprotic organic solvents which are capable of dissolving the at least bidentate organic compounds. Examples which may be mentioned are:

aromatic solvents, e.g. benzene, chlorobenzene, toluene or xylene, or halogenated hydrocarbons, e.g. chloroform.

Bases which can be used are all organic bases which are capable of deprotonating the abovementioned bidentate compounds. Specific examples are:

triethylamine, tetraalkylammonium hydroxides, e.g. tetrapropylammonium hydroxide.

Accordingly, the present invention also relates to a process, described above, wherein the base is selected from among organic amines.

The preparation of the organometallic framework materials of the present invention are prepared, for example, as follows: the organic compound is firstly dissolved in the solvent or solvent mixture, after which the metal salt is introduced, preferably while stirring continually. The introduction of the metal salt can occur by any desired method.

As soon as the solution has been homogenized, the addition of the base is commenced.

The precipitate obtained after the reaction, which comprises the organometallic framework material, is separated from the mother liquor of the reaction mixture by means of filtration, centrifugation or spray drying. To remove adhering solvent and residual base, the framework material which has been separated off in this way can be subjected to a drying step. The pressure is preferably reduced during the drying step in order to empty the pores of the organometallic framework material at least partially.

The abovementioned sequence of process steps can also be modified in a manner known to those skilled in the art or the steps can be carried out in another order.

Accordingly the present invention also relates an organometallic, microporous framework material comprising a metal ion and at least one at least bidentate organic compound coordinately bound thereto, which can be prepared by a process which comprises reacting a fluid mixture, e.g. a solution or suspension, comprising a metal salt with at least one at least bidentate organic compound capable of coordination to metal ions in the presence of at least one base and a solvent, where the solvent comprises at least one cyclic amide (lactam) and/or at least one cyclic ester (lactone).

The organometallic framework materials obtained according to the present invention contain micropores which, for the present purposes, are pores having a diameter of 2 nm or below, in accordance with the definition in Pure Applied Chem. 45, p. 71 ff., in particular p. 79, (1976). The presence of micropores can be seen from the sorption measurements for determining the nitrogen uptake capacity of the organometallic framework materials at 77K in accordance with DIN 66131, 66134. Here, the typical isotherm having the type I shape indicates the presence of micropores.

The calculated specific surface areas according to the Langmuir model (DIN 66131, 66134) are preferably above 5 m$^2$/g, more preferably above 50 m$^2$/g, in particular above 500 m$^2$/g, and can extend into the range above 2 000 m$^2$/g.

The organometallic framework materials of the present invention are used, in particular, as adsorbents, desiccants, flame retardants, storage materials or depot materials for active substances sensor material, pigment, electronic component or as catalysts, in particular as catalysts where they can be used in a broad range of applications.

Application areas for catalysts are, in particular:

oxidations, reductions, ring opening reactions, C—C coupling reactions and epoxidations, C—C bond formations such as alkylations, acylations; addition reactions such as carbonylations, aminations, hydrations, etherifications, alkoxylations; elimination reactions such as decarbonylations, decarboxylations, dehydrations; dehydrogenations and hydrogenations, isomerizations, C—C bond cleavages such as cracking and hydrocracking; reforming; oligomerizations, polymerizations; catalytic purification of waste gas and wastewater, photocatalysis.

Accordingly the present invention also relates to a process for the reaction of at least one organic compound, in which the organic compound is brought into contact with at least one catalyst according to the invention.

When used as catalysts, the organometallic framework materials of the present invention are particularly advantageous because their catalyst performance can be varied or tailored by varying the metal and/or the at least bidentate organic compound capable of coordination to metal ions. Thus, for example, reactions of C—C triple bonds can be catalyzed by the zinc-containing organometallic framework materials of the present invention. The catalyst of the present invention is suitable for use in a process for preparing compounds of the formula I or II

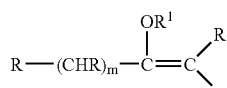

I

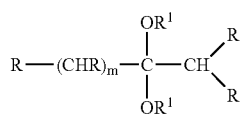

II where R$^1$ is hydrogen or an aliphatic, cycloaliphatic, araliphatic, aromatic or heterocyclic radical or an acyl radical, where the substituents may bear further substituents which do not react with acetylenes or allenes, the radicals R are, independently of one another, hydrogen or aliphatic, cycloaliphatic, araliphatic, aromatic or heterocyclic radicals which may be joined to one another to form a ring and m is 0 or 1, by addition of compounds of the formula III

R$^1$OH            III onto acetylenes or allenes of the formula IV or V

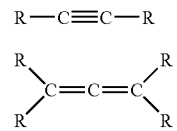

IV

V where R$^1$ and R are as defined above, in the gas, liquid or supercritical phase at elevated temperature.

Suitable starting materials for the reaction are any alkynes or allenes or mixtures thereof. However, use is generally made of acetylenes and allenes having from 2 to 8 carbon atoms or from 3 to 8 carbon atoms which are readily available in industry. Particular preference is given to propyne and allene and, in particular, hydrocarbon streams in which these are present.

The hydroxyl-containing compound R$^1$OH can be water, any alcohol, a phenol or a carboxylic acid. In general, preference is given to alcohols, in particular alkanols having from 1 to 16 carbon atoms, monocyclic phenols and low molecular weight carboxylic acids, e.g. those having from 1 to 16 carbon atoms. Particular preference is given to lower alcohols, in particular methanol.

The addition reaction of the hydroxyl-containing compounds is carried out in the presence of the heterogeneous catalyst in the gas, liquid or supercritical phase either over a fixed bed or in a fluidized bed at from 25 to 400° C., preferably from 100 to 250° C. and particularly preferably from 120 to 200° C., and pressures which depend on the starting material used, typically from 0.1 to 100 bar, in particular from 0.8 to 20 bar (or pressures based on the sum of the partial pressures of the starting materials).

Thus, for example, reaction of propyne or allene with methanol can selectively form, depending on the reaction conditions, 2-methoxypropene or 2,2-dimethoxypropane. The enol ethers of the formula I and the dialkoxy compounds of the formula II which are obtainable according to the present invention are valuable intermediates for preparing active compounds and fragrances. The enol ethers in particular are sought-after starting materials, e.g. for preparing γ, δ-unsaturated ketones as intermediates for the preparation of isophytol.

If the enol ethers in particular are to be obtained, the compounds of the formula II can be converted in a manner known per se into the corresponding enol ethers of the formula I by elimination of one mol of R$^1$OH. Numerous methods for this are known from DE-A-35 35 128, DE-A-37 22 891, DE-A-38 04 162, Chemical Abstracts, vol. 94(19); 156 241 f and DE-A-19544450.

Further details regarding the method of preparing the abovementioned compounds may be found in EP-A 1 050 510, whose relevant contents are hereby wholly incorporated by reference into the present application.

Likewise, vinyl esters can be prepared from the corresponding acid and acetylene, so that the activation of substituted acetylenes or allenes is generally possible by methods known to those skilled in the art.

Other metals, for example Cu, Pd, Au, Ru, Ni, Rh, Co and Pt, make it possible to catalyze hydrogenation and dehydrogenation reactions, including the conversion of methanol into hydrogen, for instance in fuel cell applications.

Owing to their wide variability, the organometallic framework materials can also generally be used in oxidation, epoxidation and reduction reactions if the metal chosen as component of the framework is a metal which can easily change its oxidation state, as is known, for example, in the case of many transition metals.

Apart from variation of the metal component of the framework, the catalytic behavior can also be controlled via modification of the organic component. If, for example, carboxylic acid, sulfonic acid, trifluorosulfonic acid or other acidic groups are introduced into the organic component, the resulting organometallic framework material can be used as heterogeneous solid-state acid in isomerizations, esterifications, etherifications, alkoxylations, hydrations, dehydrations, ring closure reactions and ring opening reactions or C—C coupling reactions.

Further reactions which may be mentioned are:

C—C bond formation reactions such as alkylations, acylations; addition reactions such as carbonylations, aminations, hydrations; elimination reactions such as decarbonylations, decarboxylations; dehydrations and hydrogenations; C—C bond cleavages such as cracking and hydrocracking; reforming; oxidations and epoxidations; oligomerizations, polymerizations; catalytic purification of waste gas and wastewater, photocatalysis.

If the organic component is provided with amine groups or, for example, dicarboxylates of pyridine are used as component, the use of these materials for basic catalysis becomes possible.

If alkyl-substituted aromatic dicarboxylic acids are used as organic component, it becomes possible to prepare organometallic framework materials which are later suitable for forming hydroperoxides on the alkyl chains by means of air, in order to use these peroxides for the heterogeneously catalyzed selective epoxidation of olefins.

As a result of the high surface area of the organometallic framework materials and their porosity, they can also be employed as adsorbents, desiccants, flame retardants, storage materials and depot materials for retarded liberation of pharmaceuticals.

Furthermore, these materials can, owing to their high porosity and surface area, be used as sensors or in sensors for, for example, gas detection or in application areas such as "chemistry on a chip".

The compounds can also be employed in or as electronic components or functional materials.

Depending on the application, the organometallic framework materials of the present invention can be used in powder form or shaped into extrudates, pellets, granules, rings, etc., in a reactor or can be applied to supports, for instance as coatings on distillation packing or honeycombs and knitted meshes made of metal or polymers. The reactions can, depending on the application, be carried out in a liquid, gaseous or supercritical phase.

Furthermore, all shaping and processing methods known from the plastics field can be employed, e.g. extrusion, coextrusion and incorporation into polymer blends.

BRIEF DESCRIPTION OF THE DRAWING

The FIGURE is a nitrogen type I isotherm typical of microporous materials.

The following examples illustrate the invention.

EXAMPLES

Example 1

In a reaction flask, 24.9 g of terephthalic acid were dissolved in 43.6 g of 1-methyl-2-pyrrolidone together with 8.6 g of chlorobenzene and 24.9 g of dimethylformamide and the mixture was brought to 70° C. while stirring. 52.2 g of zinc nitrate were added to this solution. After one hour, 30 g of triethylamine were added to this suspension, likewise at 70° C. The resulting solution was stirred at 70° C. for another 2 hours. The white zinc terephthalate framework material which had precipitated was filtered off and dried at ambient temperature, and subsequently baked at 200° C. The weight loss resulting from the two drying steps was 23% by weight. The yield, based on the amount of zinc used, was 87%.

The measurement of the specific surface area was carried out volumetrically using an instrument from Micromeritics (ASAP 2000) and gave a value calculated according to the Langmuir model of 1 063 m$^2$/g.

Example 2

1 320 g of 1-methyl-2-pyrrolidone were placed in a reaction flask and admixed over a period of 30 minutes with 64.2 g of terephthalic acid. 87.6 g of copper nitrate were added to this solution over a period of one hour while stirring continually and the mixture was homogenized. Finally, 81 g of triethylamine were added over a period of two hours and the mixture was stirred for another one hour.

The product was filtered off and washed with about 2 liters of water and dried at 150° C. in a vacuum drying oven.

The yield, based on the amount of copper used, was 88%.

A recording of the nitrogen isotherms (see FIGURE) at 77 K shows the type I isotherms typical of microporous materials up to p/p° <0.9.

The specific Langmuir surface area calculated therefrom is 334 m$^2$/g.

Example 3

Preparation of Vinyl 4-tert-butylbenzote 2.5 g of the catalyst prepared in example 1 together with 100 g of 1-methyl-2-pyrrolidone were placed in an autoclave and admixed with 40 g of 4-tert-butylbenzoic acid. After the autoclave had been pressurized with 5 bar of nitrogen, it was heated to 180° C. and 20 bar of acetylene were subsequently introduced and the pressure was maintained for 24 hours by introduction of further amounts. The resulting reaction mixture was analyzed by means of GC and indicated a conversion of 94% of the acid used and a selectivity of 83% to vinyl 4-tert-butylbenzoate.

Example 4

Preparation of 2-methoxypropene 55 g of a catalyst prepared as described in example 1 in pellet form were installed in a differential circulation reactor. 1.5 g/h of a liquid stream (10:1 mixture of methanol/cyclohexane) were fed in by means of an HPLC pump. Propyne was introduced at a gas flow rate of 6 g/h at 250° C. The propyne conversion was 30% and selectivity to 2-methoxypropene was 80%.

When the experiment was repeated without catalyst, no reaction of the propyne was observed.

We claim:

1. A process for preparing an organometallic framework material comprising:

reacting a fluid mixture comprising a metal salt with at least one bidentate organic compound capable of coordinating to metal ions in the presence of at least one base and a solvent, wherein the solvent comprises at least one cyclic amide (lactam) and/or at least one cyclic ester (lactone).

2. The process as claimed in claim 1, wherein the metal salt is selected from the group consisting of metal salts of zinc, copper, cobalt, nickel, palladium, platinum, ruthenium, rhenium and mixtures of two or more thereof.

3. The process as claimed in claim 1, wherein the base is at least one organic amine.

4. The process as claimed in claim 1, wherein the organic compound is selected from the group consisting of substituted and unsubstituted, monocyclic and polycyclic aromatic dicarboxylic acids containing at least one heteroatom.

* * * * *

UNITED STATES PATENT AND TRADEMARK OFFICE
CERTIFICATE OF CORRECTION

PATENT NO. : 7,119,219 B2 Page 1 of 1
APPLICATION NO. : 10/469826
DATED : October 10, 2006
INVENTOR(S) : Ulrich Mueller et al.

It is certified that error appears in the above-identified patent and that said Letters Patent is hereby corrected as shown below:

Column 7, Claim 1, line 2, "least one bidentate organic"
should read -- least one at least bidentate organic --.

Signed and Sealed this

Twentieth Day of March, 2007

JON W. DUDAS
*Director of the United States Patent and Trademark Office*